United States Patent [19]
John et al.

[11] Patent Number: 5,654,444
[45] Date of Patent: Aug. 5, 1997

[54] PREPARATION OF 5-HYDROXY-4-METHYL-2(5H)-FURANONE

[75] Inventors: Michael John, Lambsheim; Walter Dobler, Heidelberg; Joachim Paust, Neuhofen, all of Germany

[73] Assignee: BASF Aktiengesellschaft, Ludwigshafen, Germany

[21] Appl. No.: 621,035

[22] Filed: Mar. 22, 1996

[30] Foreign Application Priority Data

Mar. 27, 1995 [DE] Germany .................. 195 10473.0

[51] Int. Cl.$^6$ ................................ C07D 307/60
[52] U.S. Cl. ................................ 549/313
[58] Field of Search ................................ 549/313

[56] References Cited

PUBLICATIONS

Geoffrey K. Cooper, et al. "Convenient Synthesis of the 2–Methyl–4–Hydroxybut–2–Enolide Moiety of Strigol", *Journal of Organic Chemistry*, vol. 44, No. 19, 1979, pp. 3414–3416.

J.J. Bourguignon, et al. "Lactone Chemistry. Synthesis of β–Substituted, γ–Functionalized Butanolides and Butenolides and Succinaldehydic Acids from Glyoxylic Acid", *Journal of Organic Chemistry*, vol. 46, 1981, pp. 4889–4894.

Wiley et al., J.A.C.S., vol. 78, pp. 808–810 (1956).

A. W. Johnson et al. "The Preparation of Synthetic Analogues of Strigol", *Journal of the Chemical Society, Perkin Transactions 1*, No. 6, (1981), pp. 1734–1743 and 1735.

Database WPI, Week 9435, *Derwent Publications Ltd.*, London, GB; AN 94–283338 (1994).

*Primary Examiner*—Bernard Dentz
*Attorney, Agent, or Firm*—Oblon, Spivak, McClelland, Maier & Neustadt, P.C.

[57] ABSTRACT

5-Hydroxy-4-methyl-2(5H)-furanone is prepared by cyclization of alkyl β-formylcrotonates by heating with dilute aqueous hydrochloric acid or, advantageously, in the presence of dilute aqueous hydrochloric acid and catalytic amounts of methanol as solubilizer, subsequent workup of the reaction mixture by distillation and, where appropriate, isomerization of the 5-methoxy- or 5-ethoxy-4-methyl-2(5H)-furanone, which is formed as byproduct, by heating with dilute hydrochloric acid.

9 Claims, No Drawings

PREPARATION OF 5-HYDROXY-4-METHYL-2(5H)-FURANONE

The invention relates to a process, which can also be carried out industrially, for preparing 5-hydroxy-4-methyl-2(5H)-furanone (butenolide) starting from methyl or ethyl β-formylcrotonate.

Butenolide is an important $C_5$ synthon for preparing retinoids and carotenoids with a double bond in the (Z) configuration, such as 13(Z)-retinoic acid. The continuous growth in the demand for 13(Z)-retinoic acid for controlling ache or premature aging of the skin has been sufficient reason for the attempts which have been made to find an advantageous process, which can also be satisfactorily carried out industrially, for preparing butenolide.

Thus, J. Org. Chem. 46 (1981), 4889–94 discloses that it is possible by Mannich reaction of succinaldehyde with morpholine and glyoxylic acid in basic or neutral medium to prepare α,γ-dimorpholinobutanolide and α-morpholino-γ-hydroxybutanolide. It is possible to eliminate from the latter in an acidic medium the α-morpholino group, which forms butenolide. The disadvantages of this process are that it comprises several reaction stages, and large amounts of morpholine are needed as additional starting material.

Furthermore, J. Org. Chem. 44 (1979), 3414–16 discloses a process for preparing 5-hydroxy-3-methyl-2(5H)-furanone (a butenolide isomer), in which crotonaldehyde is converted in five very elaborate reaction stages into ethyl β-formylmethacrylate, and the latter is converted by heating with sulfuric acid into 5-hydroxy-3-methyl-2(5H)-furanone in 72% yield.

This process also has the disadvantages that the butenolide isomer must be prepared in six reaction stages, some of which are very elaborate, with the use of costly starting materials such as n-butyllithium and ethyl chloroformate.

It is an object of the present invention to develop a process for preparing butenolide which permits butenolide to be prepared, starting from easily obtainable starting materials in a simple manner and with good yields, in such an advantageous way that preparation on the industrial scale is also possible and advantageous.

We have found that this object is achieved by the conversion of alkyl β-formylcrotonate by heating with aqueous hydrochloric acid under specific conditions into butenolide in a very advantageous manner. This result was surprising because the cyclization of the β-formylcrotonate with dilute sulfuric acid by the process in J. Org. Chem. 44 (1979), 3414–16 results only in a mixture of the precursor, butenolide, 5-methoxy-4-methyl-2(5H)-furanone and a large number of decomposition products (see Comparative Examples 3a and 3b).

Since methyl β-formylcrotonate can be obtained in a simple manner and in good yields by aldol condensation of propanal with methyl glyoxylate, the overall process is thus advantageous and starts from commercially obtainable low-cost starting materials.

The invention therefore relates to a process for preparing 5-hydroxy-4-methyl-2(5H)-furanone of the formula I

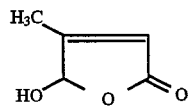

which comprises treating an alkyl β-formylcrotonate of the formula II

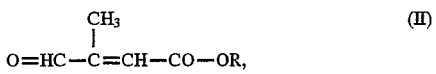

where R is methyl or ethyl, preferably methyl, with from 0.1 to 2 mol, preferably 0.6 to 1.2 mol, in particular 0.8 to 1 mol, of hydrochloric acid, in the form of 1–38% by weight aqueous hydrochloric acid, per mol of β-formylcrotonate at from 90° to 110° C. for 0.5–24 hours, preferably 0.5–4 hours.

We have furthermore surprisingly found that the butenolide yield can be considerably increased by adding a catalytic amount of methanol or ethanol as solubilizer to the reaction mixture. This was surprising because the addition of higher alkanols such as isopropanol or isobutanol did not increase the yield of the required butenolide but led to the formation of complete acetals.

It is advantageous to use methanol for the reaction of methyl β-formylcrotonate and ethanol for the reaction of the ethyl ester because, otherwise, partial transesterification takes place and thus an inhomogeneous product is formed.

The methanol or ethanol is used according to the invention in amounts of from 0.01 to 1 mol, preferably 0.01 to 0.6 mol, in particular 0.01 to 0.1 mol, per mol of alkyl β-formylcrotonate.

It is possible to use as starting compound in the process according to the invention the alkyl β-formylcrotonate in the form of a mixture of its E and Z isomers as produced in the aldol condensation of propanal with alkyl glyoxylate, because the E isomer present therein isomerizes under the reaction conditions to the Z isomer which can be cyclized.

An advantageous procedure for carrying out the process according to the invention is, for example, to mix methyl β-formylcrotonate with the aqueous hydrochloric acid and, where appropriate, methanol and to reflux the mixture, ie. to about 98° C., for the reaction time. The emulsion which initially forms dissolves within about 15 minutes after refluxing starts.

The reaction time is generally from 0.5 to 24 hours, preferably 0.5 to 4, in particular 0.5 to 3, hours.

The reaction mixture can be worked up by removing water, methanol and hydrochloric acid by distillation under reduced pressure, and then the butenolide can be obtained by distillation from the mixture which consists predominantly of the required butenolide and 5-methoxy-4-methyl-2(5H)-furanone as byproduct.

The 5-methoxy-4-methyl-2(5H)-furanone which is formed as byproduct can also be about 90% converted into the required butenolide by heating with about 0.1–1.2 mol, preferably about 1 mol, of dilute hydrochloric acid per mol of the 5-methoxy compound at from 90° to 110° C., preferably 95° to 100° C., which means that overall an almost complete conversion of the β-formylcrotonate is possible by the process according to the invention.

The dilute hydrochloric acid used in this case is also 1–38% by weight, preferably 2–20% by weight, in particular about 3–10% by weight, aqueous hydrochloric acid.

However, the process according to the invention is particularly advantageous when, after the cyclization, essentially only methanol, water and part of the hydrochloric acid are removed from the reaction mixture by distillation under reduced pressure, and the crude product, which still contains hydrochloric acid, is subsequently heated at from 90° to 110° C. for 0.25–8 hours, preferably 0.3–6 hours, during which the 5-alkoxy-4-methyl-2(5H)-furanone present in the reaction mixture is converted into the required butenolide.

The process according to the invention is very particularly advantageous when methyl β-formylcrotonate is refluxed in the presence of from 0.01 to 0.6 mol of methanol and about 0.8–1.2 mol of hydrochloric acid in the form of approximately 2–20% by weight aqueous hydrochloric acid per mol of methyl β-formylcrotonate for 0.5–4 hours, subsequently essentially methanol and water, besides part of the hydrochloric acid, are removed by distillation under reduced pressure, and the crude product, which still contains hydrochloric acid, is then heated at from 90° to 110° C. under a pressure which is finally reduced to 0.6 mbar for about 2 hours. This means in practice that the crude product which still contains hydrochloric acid is heated at 90°–110° C. under a pressure which is reduced, for example, by a vapor pump until the pressure has adjusted to about 0.6 mbar.

Butenolide is obtained in this way directly in a one-pot reaction in a yield of up to 96% of theory on workup by distillation.

The process according to the invention can be used to prepare butenolide, which is in demand for preparing rentinoids and carotenoids with the (Z) configuration, in a manner which is also industrially simple and in very good yields from readily obtainable starting materials.

EXAMPLE 1

Cyclization in the presence of methanol 409.2 g (3.124 mol) of methyl β-formylcrotonate were mixed with 10 g (0.312 mol) of methanol and 1366.8 g (1.874 mol) of 5% strength HCl and refluxed at 98° C. for 2 hours (h). The emulsion which was initially present dissolved within 15 minutes after refluxing started. Analysis by gas chromatography (GC) of the resulting crude product showed 12% 5-methoxy-4-methyl-2(5H)-furanone and 87.1% butenolide. The reaction product with this composition was concentrated at 90° C. and 10 mbar to remove water, methanol and HCl before fractional distillation was carried out under 1 mbar to remove the 5-methoxy-4-methyl-2(5H)-furanone occurring as byproduct.

Distillation under 1 mbar afforded 6.75 g of fraction 1, 328.9 g of fraction 2 and 9.72 g of residue.

GC analysis (25 m OV1701, 50/10/240) showed the following composition of the fractions:

Fraction 1:
 34.9% 5-methoxy-4-methyl-2(5H)-furanone
 63.8% butenolide
Fraction 2:
 97% butenolide Thus, based on the amount of butenolide isolated (fraction 2), the yield was 92% of theory.

To improve the overall yield, the 5-methoxy-4-methyl-2 (5H)-furanone occurring as byproduct was converted into the required butenolide. This was done by refluxing 81.86 g (0.64 mol) of 5-methoxy-4-methyl-2(5H)-furanone with 465.9 g (0.64 mol) of 5% by weight HCl for 2.5 h. GC analysis of the reaction product showed a composition of 10.1% precursor and 89.1% butenolide, so that overall almost complete conversion of the methyl β-formylcrotonate originally employed is possible.

EXAMPLE 2

Cyclization in the absence of methanol 102.3 g of methyl β-formylcrotonate and 38.4 g of 38% strength aqueous hydrochloric acid were refluxed together for 3 h.

GC analysis of the resulting crude products showed 53% 5-methoxy-4-methyl-2(5H)-furanone and 42% of required butenolide.

The crude product obtained in this way was concentrated under 10 mbar to remove water and hydrochloric acid and then fractionally distilled.

The resulting 5-methoxy-4-methyl-2(5H)-furanone was converted by heating with 5% aqueous hydrochloric acid as in Example 1 into the required butenolide.

The overall yield of butenolide was 81% of theory.

EXAMPLE 3

(Comparative Examples)

a) Without methanol addition 102.3 g of methyl β-formylcrotonate were refluxed together with 200 ml of 4N $H_2SO_4$ for 3 h. GC analysis of the resulting crude product showed the following composition:

25% unreacted precursor,
18% butenolide,
19% 5-methoxy-4-methyl-2(5H)-furanone and
38% of a large number of decomposition products.

b) With methanol addition

The procedure was as in Example 3a but with the addition of 32 ml of methanol. GC analysis of the resulting crude product showed the following composition:

43% unreacted precursor,
9% butenolide,
22% 5-methoxy-4-methyl-2(5H)-furanone and
26% of a large number of decomposition products.

EXAMPLE 4

512 g (3.9 mol) of methyl β-formylcrotonate were mixed at room temperature with 12.5 g (0.39 mol) of methanol and 1.4 kg of 10% strength aqueous hydrochloric acid and the mixture was refluxed for 2 h and then cooled to room temperature. Subsequently, the volatiles present were removed by distillation under reduced pressure (10–20 mbar) at 90° C., and the reaction mixture, which still contained hydrochloric acid, was heated at about 90° C. under pressure reduced by a vapor pump until the pressure adjusted to about 0.6 mbar, which took about 2 h.

It was found by GC analysis that butenolide was obtained in this one-pot reaction in a yield of 96% of theory and in a purity of 96–97%.

EXAMPLE 5

As in Example 4, 566.6 g (3.91 mol) of ethyl β-formylcrotonate were mixed with 17.9 g (0.39 mol) of ethanol and 1.4 kg of 10% strength aqueous hydrochloric acid, and the mixture was refluxed for 2 h and then cooled to room temperature. Removal of the volatiles by distillation and heating of the reaction mixture at 90° C. under reduced pressure for 2 hours as in Example 4 resulted in butenolide in a yield of 93% of theory and a purity of 96–98%.

We claim:

1. A process for preparing 5-hydroxy-4-methyl-methyl-2 (5H)-furanone of the formula I

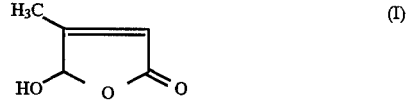

which comprises treating alkyl β-formylcrotonate of the formula II

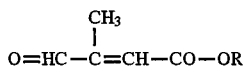

where R is methyl or ethyl, in the presence of from 0.01 to 1 mol of methanol or ethanol per mol of β-formylcrotonate, with from 0.1 to 2 mol of hydrochloric acid, in the form of 1–38% by weight aqueous hydrochloric acid, per mol of β-formylcrotonate at from 90° to 110° C. for 0.5 to 24 hours.

2. A process as claimed in claim 1, wherein methyl β-formylcrotonate is used as alkyl β-formylcrotonate.

3. A process as claimed in claim 1, wherein the β-formylcrotonate of the formula II is heated with from 0.6 to 1.2 mol of aqueous hydrochloric acid.

4. A process as claimed in claim 1, wherein the β-formylcrotonate of the formula II is heated with 2–20% by weight aqueous hydrochloric acid.

5. A process as claimed in claim 1, wherein the alkyl β-formylcrotonate is heated with the aqueous hydrochloric acid in the presence of from 0.01 to 0.6 mol of methanol per mol of β-formylcrotonate.

6. A process as claimed in claim 2, wherein the methyl β-formylcrotonate is refluxed in the presence of from 0.01 to 0.6 mol of methanol and about 0.8–1.2 mol of hydrochloric acid in the form of approximately 2–20% by weight aqueous hydrochloric acid per mol of methyl β-formylcrotonate for 0.5–4 hours.

7. A process as claimed in claim 1, wherein the 5-alkoxy-4-methyl-2(5H)-furanone formed as byproduct in the reaction is isolated and converted by heating with dilute hydrochloric acid into 5-hydroxy-4-methyl-2(5H)-furanone of the formula I.

8. A process as claimed in claim 1, wherein methyl β-formylcrotonate is refluxed in the presence of from 0.01 to 0.6 mol of methanol and about 0.8–1.2 mol of hydrochloric acid in the form of approximately 2–20% by weight aqueous hydrochloric acid per mol of methyl β-formylcrotonate for 0.5–4 hours, subsequently essentially methanol and water are removed by distillation under reduced pressure, the crude product, which still contains hydrochloric acid, is heated at from 90° to 110° C. for 0.25–6 hours, and the reaction mixture treated in this way is fractionally distilled.

9. A process as claimed in claim 1, wherein the methyl β-formylcrotonate is refluxed in the presence of from 0.01 to 0.6 mol of methanol and about 0.8–1.2 mol of hydrochloric acid in the form of approximately 2–20% by weight aqueous hydrochloric acid per mol of methyl β-formylcrotonate for 0.5–4 hours, subsequently essentially methanol and water are removed by distillation under reduced pressure, the crude product, which still contains hydrochloric acid, is heated at from 90° to 110° C. under a pressure which is finally reduced to 0.6 mbar for about 2 hours, and the reaction mixture treated in this way is fractionally distilled.

* * * * *